United States Patent [19]

Akers et al.

[11] Patent Number: 4,816,415
[45] Date of Patent: Mar. 28, 1989

[54] CANNABINOID DETECTION METHOD

[75] Inventors: Susan Akers, Mantua; Raymond F. Akers, Jr., Cherry Hill, both of N.J.

[73] Assignee: Analytical Innovations, Inc., Cherry Hill, N.J.

[21] Appl. No.: 55,438

[22] Filed: May 29, 1987

[51] Int. Cl.$^4$ .................... G01N 21/78; G01N 33/94
[52] U.S. Cl. .................................. 436/93; 436/169; 436/178; 436/901
[58] Field of Search .................. 436/92, 93, 96, 98, 436/131, 164, 169, 170, 178, 901

[56] References Cited

U.S. PATENT DOCUMENTS

| | | |
|---|---|---|
| 2,865,718 | 12/1958 | Fowler . |
| 3,275,416 | 9/1966 | Zaar et al. ............................ 436/98 |
| 3,598,533 | 8/1971 | Tomioka . |
| 3,625,652 | 12/1971 | Fujimoto et al. ................ 436/92 X |
| 3,802,842 | 4/1974 | Lange . |
| 3,901,657 | 8/1975 | Lightfoot . |
| 3,915,639 | 10/1975 | Friedenberg .................... 436/901 X |
| 3,966,410 | 6/1976 | Jahnsen ........................... 436/901 X |
| 4,104,027 | 8/1978 | Carroll ................................ 436/92 |
| 4,196,167 | 4/1980 | Olson . |
| 4,393,141 | 7/1983 | Schlueter et al. ............. 436/178 X |
| 4,438,067 | 3/1984 | Siddiqi . |
| 4,680,120 | 7/1987 | Ramsden et al. .............. 436/901 X |
| 4,680,121 | 7/1987 | Ramsden et al. .............. 436/901 X |

FOREIGN PATENT DOCUMENTS 1426177 2/1976 United Kingdom .................. 436/92

OTHER PUBLICATIONS

Lau-Cam et al, J. of Pharmaceutical Sciences, vol. 68, No. 8, pp. 976-978, 1979.
De Faubert Maunder, Bulletin on Narcotics, vol. XXVI, No. 4, pp. 19-26, 1974.
De Faubert Maunder, J. of Chromatography, vol. 100, pp. 196-199, 1974.
De Faubert Maunder, J.A.P.A., vol. 7, pp. 24-30, 1969.
De Faubert Maunder, J. Pharm. Pharmac., vol. 21, pp. 334-335, 1969.

Primary Examiner—Barry S. Richman
Assistant Examiner—Robert J. Hill, Jr.
Attorney, Agent, or Firm—Steele, Gould & Fried

[57] ABSTRACT

A method for detecting cannabinoids in body fluids which comprises filtering body fluids through a cellulosic filtering means treated with a binding agent for cannabinoids and the filtering means. The binding agent is an arylcarboxylic acid. The cannabinoids are then treated with a subsequent reagent to produce a color reaction. A device for detecting cannabinoids is also disclosed which contains the filtering means treated with the binding agent so as to concentrate the cannabinoid prior to reaction with a suitable indicator.

8 Claims, 1 Drawing Sheet

CANNABINOID DETECTION METHOD

FIELD OF THE INVENTION

The present invention relates to testing methods used to ascertain the presence of certain types of narcotics or drugs in body fluids. More particularly, the invention is concerned with a method for concentrating such drugs as cannabinoids that may be present in urine and detecting their presence colorimetrically by a suitable chemical reagent.

BACKGROUND OF THE INVENTION

Due to the wide spread use of controlled substances or narcotics such as cannabinoids (marijuana), cocaine, amphetamines, and the like, it has become desirable to institute drug testing of athletes and others which are engaged in an occupation involving a public trust or in which an injury can occur if the party is not completely alert. Testing of athletic teams, bus drivers, etc. involve large group testing which must be conducted quickly, accurately and inexpensively. A highly sensitive, easily-read test for the detection of narcotics such as cannabinoids in urine would be extremely helpful in a drug program. Narcotic screening has become extensive practice in industry, business, the Armed Forces, schools and in the courts and prison systems. Such screening is used both as a pre-employment procedure and as a monitoring tool. The present methods for the detection of cannabinoids in urine are relatively costly and time consuming and must, in general, be performed by qualified personnel in well-equipped laboratories. It would be highly desirable and useful to be able to carry out a quick test of the presence of narcotics in urine by a person who is untrained in chemical laboratory manipulations and who does not have at his disposal the instrumentation and laboratory equipment required in the prior methods.

U.S. Pat. No. 4,196,167 of Olsen discloses a method for detecting cannabis presence using a swab.

Clarke, "Isolation and Identification of Drugs", The Pharmaceutical Press, London, 1969, pp 431–432, which is herein incorporated by reference discloses chemical reagents which can be utilized in the detection of common narcotic substances.

OBJECTS AND SUMMARY OF THE INVENTION

It is an object of this invention to provide a method for the detection of cannabinoids and the like which are present in minute amounts in body fluids.

It is another object of the present invention to provide a method which is broadly adaptable to a wide variety of colorimetric reactions and which will increase the sensitivity of the color reaction in cannabinoid testing by several fold over the corresponding solution reaction.

It is a further object of this invention to provide a method capable of rapidly and colorimetrically detecting, in the hands of untrained people, extremely minute amounts of a cannabinoids in urine.

These and other objects of the invention can be achieved by providing a cellulosic filtering means which is treated with a binding agent and a suitable chemical detecting reagent. The filtering means serves to collect, and therefore to concentrate any cannabinoids which may be present in the body fluids and which may be too dilute to be detected by conventional techniques. It is particularly advantageous in detecting cannabinoid use where the drug user has abstained from drug use for a few days in anticipation of the test.

The filtering means of the present invention in essence filters cannabinoids from urine that is passed through the means by binding these drugs through the binding agent. The chemical reagent for the cannabinoid is then poured onto the filtering means, and a characteristic color appears which indicates that a cannabinoid is present.

Advantageously, the filtering means is used in connection with a funneling means so as to facilitate collection and concentration at the disk. The body fluid or urine sample is first poured onto a disk impregnated with a suitable binding agent, and then a suitable chemical reagent is poured over the disk. A characteristic color appears on the disk indicating whether or not a cannabinoid is present.

The binding agent which may be utilizable is an arylcarboxylic acid, preferably, biphenyl and triphenyl carboxylic acids. In operation, the carboxylic acid group reacts with the free hydroxyl group of the cellulosic filter. The cannabinoids are then bound to the phenyl group of the binding agent and are held on the filter as the body fluids are filtered so as to concentrate the cannabinoids.

Other objects and a fuller understanding of the invention will be had by referring to the following description and claims of a preferred embodiment, taken in conjunction with the accompanying drawings, wherein like reference characters refer to similar parts throughout the several views.

BRIEF DESCRIPTION OF THE DRAWINGS

FIG. 3 is a side sectional view of a disposable test funnel having a reagent impregnated portion.

DESCRIPTION OF THE PREFERRED EMBODIMENT OF THE INVENTION

Figure 1:
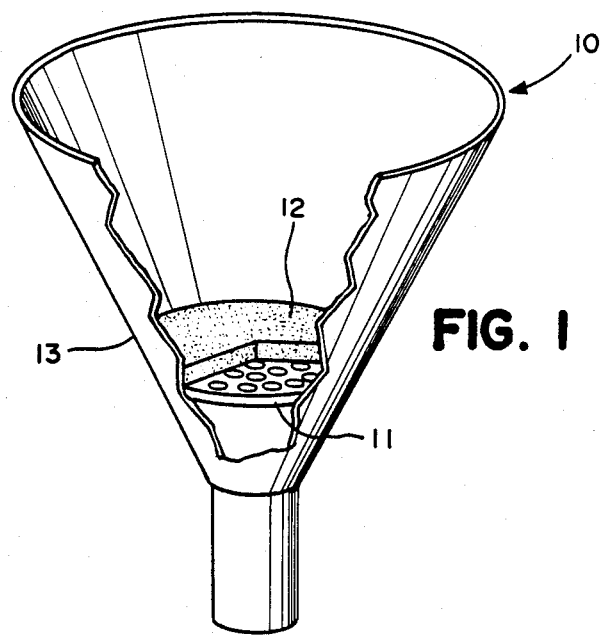
FIG. 1 is a perspective view of the testing device of the invention.

Although specific terms are used in the following description for the sake of clarity, these terms are intended to refer only to the particular structure of the invention selected for illustration in the drawings, and are not intended to define or limit the scope of the invention.

As illustrated in Fig. 1, the test device of the invention may comprise a means 10 for collecting and concentrating body fluids, for example, urine, for testing the presence of cannabinoids. The means 10 may, for example, comprise a funnel 13 having a perforated support 11 on which there is placed a cellulosic disk 12. A binding agent is placed into solution and poured through the funnel 13 so as to bind on the disk 12. The test fluid which is suspected of containing a cannabinoid is then passed through the funnel 13 whereby the cannabinoid interacts with the binding agent and remains on the disk. A suitable test reagent for the cannabinoid, for example, Fast Green or Fast Blue BB salt in a basic aqueous solution is poured through the funnel and the development of a red color on the disk indicates the presence of a cannabinoid.

The disk 12 can consist of cellulosic filter paper or regularly woven cellulosic filaments in the form of a fabric with weft and warp threads or can be in the form of an unwoven fabric. It is also possible to use thin felt-or fleece-like meshwork in which the fibre structure is not uniform, provided that they have the necessary neutral color and stability. It is preferred to use natural cellulosic material or synthetic resin fabric of monofile or spun filaments which can consist of cellulose materials, for example cotton, cellulose, flax or sisal. The cellulosic resins which are employed are cationic and/or hydrophobic. Within the given limits, the meshwork can be varied, depending upon the color reaction of the indicator layer. Normally, a meshwork of colorless material is used. However, with colored meshwork, mixed colors with the colors of the indicator layer are obtained, which can sometimes increase the contrast. In addition, it is also possible to impregnate the meshwork with reagents which only penetrate into the indicator layer upon wetting. This separate impregnation is recommended when there is a possibility that two or more binding agents, detection reagents and/or adjuvants might react together during storage.

Figure 2:
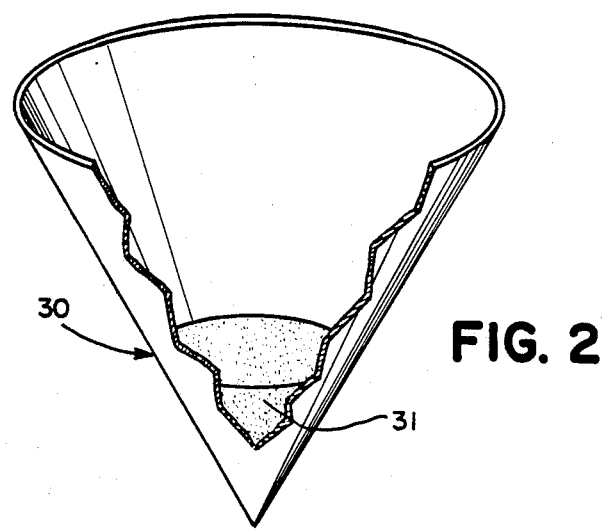
FIG. 2 is a schematic presentation of a specific embodiment of a multi-layered disk of the invention.

FIG. 2 illustrates a filter 30 which is impregnated in part 31 with a binding agent. The filter 30 is intended for use with a conventional funnel. After urine is passed through the funnel, an indicator is added and the color is observed to indicate the presence of a cannabinoid.

The indicators which are utilized to test the presence of cannabinoids are conventional and commercially available. The indicators include alkali hydroxides (Beam Test); Fast Blue BB salt (tetraazatized di-O-anisidine), Dûquenois-Negm test (vanillin acetaldelyde-ethanol in hydrochloric acid) and Fast Bourdeaux Gp salt.

From the foregoing it is believed that those familiar with the art will readily recognize and appreciate the novel concepts and features of the present invention. Numerous variations, changes and substitutions of equivalents will present themselves from persons skilled in the art and may be made without necessarily departing from the scope and principles of this invention. As a result, the embodiment described herein is subject to various modifications, changes and the like, with the scope of this invention being determined solely by reference to the claims appended hereto.

What is claimed is:

1. A method for analyzing a sample of a body fluid for the presence of cannabinoids which comprises:
    filtering a sample of a body fluid through a cellulosic filtering means which has been treated with a binding agent for said filtering means and cannabinoids so that any cannabinoids in said sample bind to said filtering means, said binding agent being an arylcarboxylic acid;
    contacting said filtering means with a color indicator for cannabinoids; and
    observing the filtering means for any color change, wherein any color change is indicative of the presence of cannabinoids in said sample.

2. The method of claim 1 wherein said arylcarboxylic acid is a bihenylcarboxylic acid.

3. The method of claim 1 wherein said arylcarboxylic acid is a triphenylcaboxylic acid.

4. The method of claim 1 wherein the body fluid is urine.

5. The method of claim 1 wherein said filtering means is a filtering disk.

6. The method of claim 1 wherein said filtering means is supported by a funnel.

7. A method for analyzing a urine sample for the presence of cannabinoids which comprises:
    filtering a sample of urine through a cellulosic filtering means which has been treated with a biphenylcarboxylic acid binding agent that binds to said filtering means and cannabinoids so that any cannabinoids in said urine sample bind to said filtering means;
    contacting said filtering means with a color indicator for cannabinoids; and
    observing the filtering means for any color change, wherein any color change is indicative of the presence of cannabinoids in said sample.

8. The method of claim 7 wherein said color indicator is selected from the group consisting of Fast Blue BB salt, Fast Green salt, and Fast Bourdeaux Gp salt.

* * * * *